United States Patent [19]

Schinabeck et al.

[11] Patent Number: 5,264,084
[45] Date of Patent: Nov. 23, 1993

[54] PROCESS FOR SEPARATING OFF ALKENES DURING METHYLCHLOROSILANE DISTILLATION

[75] Inventors: Anton Schinabeck; Berthold Haefner; Bernd Pachaly, all of Burghausen, Fed. Rep. of Germany

[73] Assignee: Wacker-Chemie GmbH, Munich, Fed. Rep. of Germany

[21] Appl. No.: 933,141

[22] Filed: Aug. 21, 1992

[30] Foreign Application Priority Data

Sep. 16, 1991 [DE] Fed. Rep. of Germany ....... 4130790

[51] Int. Cl.$^5$ ............................. B01D 3/34; C07F 7/18
[52] U.S. Cl. ................................ 203/34; 203/DIG. 6; 556/465; 556/467; 556/472
[58] Field of Search ........................... 203/34, DIG. 6; 556/472, 465, 467

[56] References Cited

U.S. PATENT DOCUMENTS

| | | | |
|---|---|---|---|
| 2,380,995 | 8/1945 | Rochow | 556/472 |
| 2,563,557 | 8/1951 | Schubert et al. | 203/71 |
| 2,755,295 | 7/1956 | Gordon | 556/467 |
| 3,359,186 | 12/1967 | Petelinkar | 203/34 |
| 3,985,781 | 10/1976 | Kötzsch et al. | 556/471 |
| 4,173,576 | 11/1979 | Seiler et al. | 556/471 |
| 4,202,831 | 5/1980 | Schlak et al. | 556/451 |

FOREIGN PATENT DOCUMENTS

| | | |
|---|---|---|
| 0411645 | 8/1990 | European Pat. Off. . |
| 0423948 | 9/1990 | European Pat. Off. . |
| 1243193 | 7/1965 | Fed. Rep. of Germany . |
| 52-18691 | 2/1977 | Japan . |

OTHER PUBLICATIONS

Chemistry and Technology of the Silicones, Academic Press, Inc., Orlando, Fla., 1968, Chapter 2.2.

Primary Examiner—Virginia Manoharan

[57] ABSTRACT

A process for separating alkenes from a methylchlorosilane mixture by adding at least a stoichiometric amount of hydrogen chloride necessary for saturating the alkenes in the methylchlorosilane mixture and thereafter removing resulting chloroalkanes by distillation.

3 Claims, 1 Drawing Sheet

PROCESS FOR SEPARATING OFF ALKENES DURING METHYLCHLOROSILANE DISTILLATION

The invention relates to a process for removing alkenes and more particularly to a process for removing alkenes during methylchlorosilane distillation. The alkenes are formed as by-products in the direct synthesis of methylchlorosilanes.

BACKGROUND OF THE INVENTION

The direct synthesis of methylchlorosilanes from silicon and methyl chloride at 250° to 300° C. by means of copper catalysts produces, in addition to the methylchlorosilanes of the general formula $Me_xSiC_4$, x having values of from 0 to 4 and Me represents a methyl group, also ethylchlorosilanes, various hy silanes, in particular $Me_yHSiCl_{3-y}$, y having values from 0 to 2, and ethyldichlorosilane ($EtHSiCl_2$) in small amounts. Furthermore, various straight-chain and branched alkanes and alkenes having up to 9 carbon atoms are also formed as impurities. The direct synthesis is described, inter alia, in W. Noll, 2nd Edition 1968, Verlag Chemie, Weinheim, Chapter 2.2.

The methylchlorosilanes are separated by distillation and freed from impurities. However, some alkenes cannot be completely removed in this manner due to their boiling point or because of the formation of azeotropic mixtures. Co-entrained alkenes, in particular branched alkenes, undergo a reversible addition reaction with hydrogen chloride upon hydrolysis of the methylchlorosilane to intermediates or end products. Due to their high boiling point, the chloroalkanes formed therefrom remain in the product and slowly release hydrogen chloride when the product is heated during its use. This hydrogen chloride causes, for example, as condensation catalyst undesirable reactions.

The most desirable product of the direct synthesis is $Me_2SiCl_2$, which can be reacted by hydrolysis and polycondensation to form silicone polymers having a variety of functional groups and structures.

An essential feature of the quality of most silicone polymers is a minimum amount of trifunctional impurities in the polymer structure. The most frequent trifunctional impurities of the $Me_2SiCl_2$ used are $MeSiCl_3$ and $EtHSiCl_2$.

Due to these impurities, the distillation of $Me_2SiCl_2$, which in most cases is carried out continuously, requires apparatuses and equipment having very high separation efficiencies, since the boiling points of the components differ only slightly.

The mode of operation and the quality control are monitored by gas chromatography. However, the $EtHSiCl_2$ content is very difficult to detect, since the GC signal is superimposed by that of trans-3-methylpentene even with optimum analysis of gas chromatographic methods. This alkene by-product of direct synthesis is very difficult to separate off despite its slightly different boiling point relative to $Me_2SiCl_2$ and even accumulates in $Me_2SiCl_2$ fractions. Table I shows the most important boiling points and concentrations of a high-quality Me2SiCl2 fraction. Hereinafter the concentrations are always by weight.

TABLE I

| Silane | Boiling point | Concentration |
|---|---|---|
| $Me_2SiCl_2$ | 70° C. | >99.9% |
| $MeSiCl_3$ | 66° C. | <1 ppm |
| $EtHSiCl_2$ | 71° C. | <1 ppm |
| trans-3-methylpentene | 68° C. | <1 ppm |

Apart from the troublesome behavior described above of co-entrained alkenes, trans-3-methylpentene elevates the analytical values of the $EtHSiCl_2$ content. This requires high reflux ratios during distillation, which lead to a high energy consumption and reduced capacity of the equipment.

Therefore, it is an object of the present invention to provide a process for removing alkenes during methylchlorosilane distillation.

SUMMARY OF THE INVENTION

The foregoing object and others which will become apparent from the following description are accomplished in accordance with this invention, generally speaking, by providing a process for removing alkenes from a methylchlorosilane mixture during methylchlorosilane distillation, in which at least a stoichiometric amount of hydrogen chloride necessary for saturating the alkenes is added to the methylchlorosilane mixture and the resulting chloroalkanes are removed by distillation.

DESCRIPTION OF THE INVENTION

Figure 1:
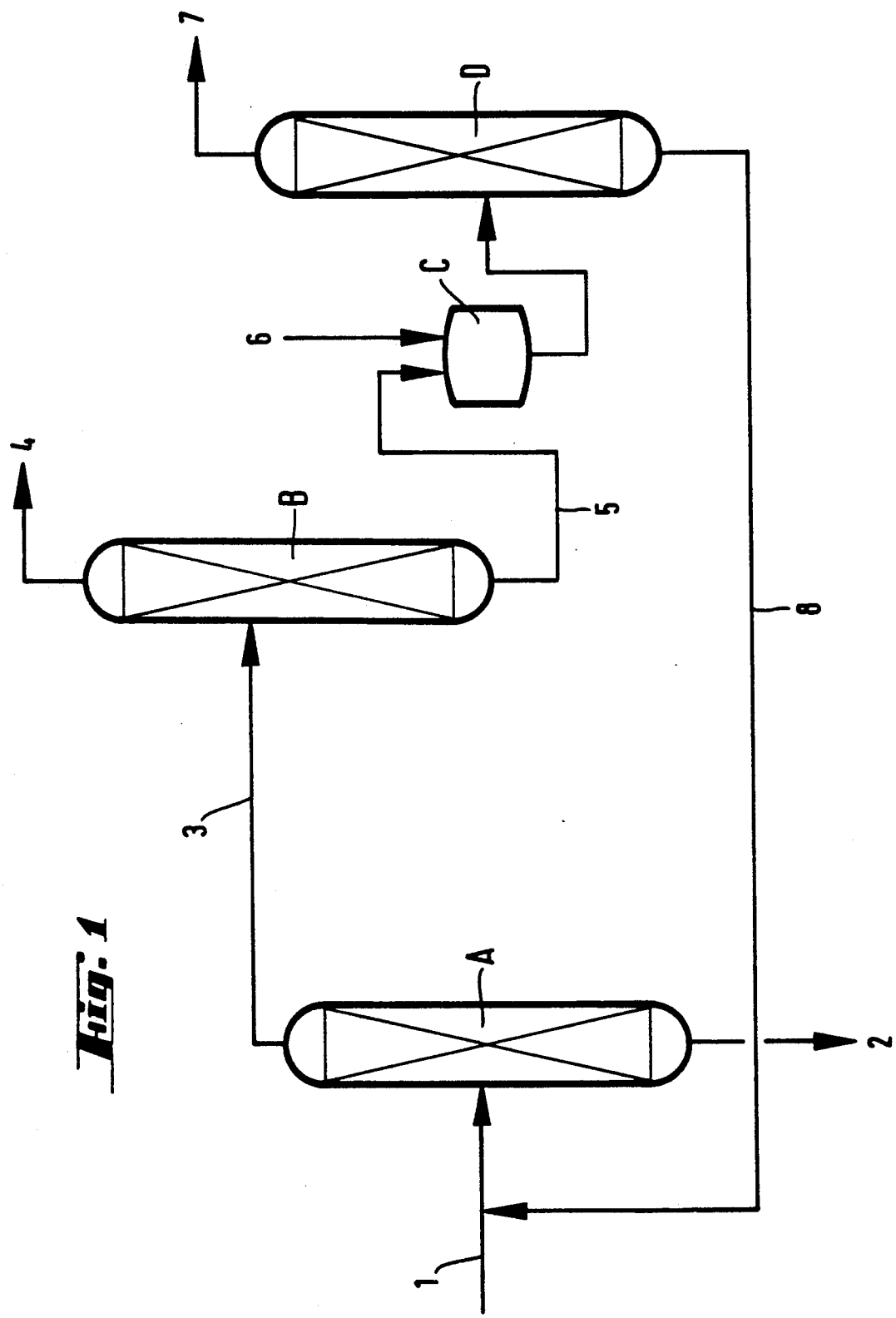
FIG. 1 is a flow diagram of a process for removing alkenes from a methylchlorosilane mixture.

In the process of this invention, the alkenes are converted into higher-boiling chloroalkanes by addition of the hydrogen chloride in the form of a gas and the high-boiling chloroalkanes are discharged at suitable points of the distillation unit. The chloroalkanes are much easier to remove by distillation than the alkenes.

In the process of this invention, at most 4 times the stoichiometric amount of hydrogen chloride necessary for saturating the alkenes is preferably added, since excess hydrogen chloride gas has to be removed from the column of the distillation unit as waste gas. Excessive amounts of hydrogen chloride reduce the separation efficiency of the distillation unit. A large excess of hydrogen chloride is therefore preferably removed from the distillation unit after the reaction with the alkenes before introducing the methylchlorosilane mixture into a distillation column.

The hydrogen chloride fed into the distillation unit does not damage methylchlorosilane distillation units generally employed because they have to be designed for exposure to traces of hydrogen chloride.

Preferably, the hydrogen chloride is fed into the distillation unit such that the alkenes dissolved in the methylchlorosilane mixture have enough time to react completely to form chloroalkanes. It is particularly advantageous if the mixture remains in a process tank for at least 5-50 hours after adding the hydrogen chloride and before separating off the chloroalkane. The residence time in the tubes of distillation units is often too short and the solubility of the hydrogen chloride in the methylchlorosilane mixture in the columns is too small to ensure complete conversion.

The removal of trans-3-methylpentene by distillation from a methylchlorosilane mixture as 3-chloro-3-methylpentane is of particular importance. The addition of hydrogen chloride produces chloro-3-methylpentane having a boiling point of 116.4° C. at 33 hPa. The purity criteria of high-quality $Me_2SiCl_2$, fraction listed above can be achieved with less expenditure of energy than without the removal of trans-3-methylpentene in accordance with this invention.

A preferred embodiment of the process of this invention is illustrated in FIG. 1. The methyl chloride free crude silane mixture from the direct synthesis, which is introduced via line 1, is separated in column A in such a manner that $Me_2SiCl_2$ and lower-boiling components having an $EtHSiCl_2$ content of less than 1 ppm can be removed at the column head and accordingly $Me_2SiCl_2$ and higher-boiling components, including $EtHSiCl_2$, at the bottom. The top product of column A is transferred to column B via line 3, and the bottom product is discharged via line 2 in order to separate off the higher-boiling components from the $Me_2SiCl_2$. In column B, the low-boiling components are removed from $Me_2SiCl_2$ and $MeSiCl_3$ via line 4. The bottom product still containing alkenes is passed to process tank C via line 5, where hydrogen chloride gas is introduced via line 6. After a residence time determined by the volume of process tank C, the mixture of $Me_2SiCl_2$ and $MeSiCl_3$, which now contains chloroalkanes, is passed to column D. There, $MeSiCl_3$ and the impurity traces which have a lower boiling point than $Me_2SiCl_2$ are removed as the top product via line 7. The bottom product contains the recovered $Me_2SiCl_2$ together with higher-boiling chloroalkanes. This bottom product is passed via line 8 to the crude silane mixture in line 1. Without addition of hydrogen chloride, an alkene cycle, including trans-3-methylpentene, is formed via lines 3, 5 and 8. This also causes elevated $EtHSiCl_2$ values in column A determined by gas chromatography.

By introducing hydrogen chloride via line 6 into process tank C, the alkenes are converted to higher-boiling chloroalkanes and discharged in the bottom of column A via line 2. This makes it possible to reduce the reflux ratio in column A and to increase the removal of bottom and top product.

In the following examples:
(a) the reference symbols refer to FIG. 1;
(b) the term "hydrocarbons" refers to the sum of alkenes, chloroalkanes and alkanes, alkanes only being present in traces;
(c) the term "removal rate" refers to the top product.

EXAMPLES

Example 1—(without hydrogen chloride)

Column A was operated continuously in such a manner that at a
bottom concentration of 300 ppm of $EtHSiCl_2$ a concentration of this component in the top product did not exceed 1 ppm. The $EtHSiCl_2$ concentration was determined by gas chromatography (FID detector). This required, at a removal rate of 6.3 tons/hour, reflux ratio of 1:18 at reflux amount of 140 m$^3$/hour column D, about 500 ppm of hydrocarbons, some of which had to be circulated in column A via line 8, occurred in the top and also in the bottom product.

Example 2—(with hydrogen chloride)

About 1 m$^3$/hour, of hydrogen chloride gas was fed into process tank C having a volume of 100 m$^3$ and a filling amount of 50% at a throughput of 1.5 tons/hour. Accordingly, the residence time of the methylchlorosilane mixture in process tank C was about 30 hour. The bottom product from column B contained about 1000 ppm of hydrocarbon. Since the hydrocarbon proportion consisted predominantly of trans-3-methylpentene, the amount of hydrogen chloride was about 2.5 times the stoichiometrically required amount.

After this time, less than 50 ppm of hydrocarbons occurred in the top product in column D. The bottom fraction returned to column A contained about 1000 ppm of chlorinated hydrocarbons and hydrocarbons. In column A, the concentration of 1 ppm of $EtHSiCl_2$ in the top product was achieved at a reflux ratio of as low as 1:7 at a reflux amount of 70 m$^3$/hour and a removal rate of 8 tons/hour.

What is claimed is:

1. A process for removing trans-3-methylpentene from a methylchlorosilane mixture having the formula $Me_xSiCl_{(4-x)}$, where Me represents a methyl group and x has a value of from 1 to 3, which comprises adding during the distillation of the methylchlorosilane mixture a stoichiometric amount of hydrogen chloride necessary for reacting with the trans-3-methylpentene present in the methylchlorosilane mixture to form 3-chloro-3-methylpentane and thereafter removing the resultant 3-chloro-3-methylpentane by distillation.

2. The process of claim 1, in which 1 to 4 times the stoichiometric amount of hydrogen chloride necessary for reacting with the trans-3-methylpentene is added.

3. The process of claim 1, in which the methylchlorosilane mixture containing trans-3-methylpentene and hydrogen chloride is stored for at least 5–50 hours in a process tank before the 3-chloro-3-methylpentane is removed by distillation.

* * * * *